United States Patent [19]

Markofsky

[11] Patent Number: 5,162,572
[45] Date of Patent: Nov. 10, 1992

[54] PROCESS FOR PREPARATION OF NITROACETATE

[75] Inventor: Sheldon B. Markofsky, Olney, Md.

[73] Assignee: W.R. Grace & Co.-Conn., New York, N.Y.

[21] Appl. No.: 810,650

[22] Filed: Dec. 19, 1991

[51] Int. Cl.$^5$ ............................................. C07C 205/00
[52] U.S. Cl. ...................................................... 560/156
[58] Field of Search ........................................ 560/156

[56] References Cited

U.S. PATENT DOCUMENTS

| | | |
|---|---|---|
| 3,026,352 | 3/1962 | Matthews . |
| 3,761,510 | 9/1973 | Sifniades . |
| 4,495,362 | 1/1985 | Honda ................................. 560/156 |
| 4,873,358 | 10/1989 | Quirk ................................... 560/156 |

OTHER PUBLICATIONS

Arndt and Rose, J. Chem. Soc., p. 6 (1935).
Finkbeiner et al., J. Org. Chem., 28, 215–217 (1963).
Kornblum et al., J. Am. Chem. Soc., 77, 6654–5 (1955).

*Primary Examiner*—Michael L. Shippen
*Attorney, Agent, or Firm*—Beverly K. Johnson

[57] ABSTRACT

An improved process for preparing alkyl nitroacetates by the gradual addition of nitric acid to a reaction vessel having therein a solution of alkyl nitroacetate and a carboxylic acid anhydride, optionally in the presence of an acid catalyst, at low temperatures to form an alkyl nitroacetoacetate intermediate which can thereafter be cleaved with a nucleophile to form an alkyl nitroacetate.

27 Claims, No Drawings

PROCESS FOR PREPARATION OF NITROACETATE

FIELD OF INVENTION

This invention relates to an improved process for preparing alkyl nitroacetates. More particularly, this invention relates to a process for preparing alkyl nitroacetates by gradually adding nitric acid to a solution of alkyl acetoacetate and a carboxylic acid anhydride to form an intermediate alkyl nitroacetoacetate and thereafter cleaving the intermediate with a nucleophile.

BACKGROUND OF THE INVENTION

Alkyl nitroacetates are known compounds which are useful as intermediates to prepare various pharmaceutical and pesticidal products. Several methods are known to prepare alkyl nitroacetates, but none of them has proven commercially successful due to their high costs or potential health hazard.

U.S. Pat. No. 3,026,352 discloses the preparation of ethyl nitroacetate by self condensation of 2 mols of nitromethane in the presence of 4 mols of potassium hydroxide to form the dipotassium salt of nitroacetic acid followed by acidification and esterification.

Finkbeiner et al. have disclosed in J. Org. Chem., 28, 215-217 (1963) a process whereby nitromethane is treated with an excess of magnesium methyl carbonate to form the magnesium chelate of nitroacetic acid followed by esterification with a strong acid.

Kornblum et al. reported in J. Am. Chem. Soc., 77, 6654-5 (1955) that they prepared ethyl nitroacetate by reacting ethyl iodoacetate with silver nitrite.

Relatively high yields of the desired alkyl nitroacetate are prepared by these methods, but they are not suitable as a commercial route to formation of alkyl nitroacetate compounds due to the high cost of starting materials such as nitromethane, magnesium and silver.

Another route was disclosed by early researchers Bouveault and Wahl, Bull. Soc. Chim. France, 31, 847-54 (1904), whereby ethyl acetoacetate was reacted with absolute nitric acid in acetic anhydride at 30°-35° C., but low yields of ethyl nitroacetate were reported. This work was later confirmed by Arndt and Rose in J. Chem. Soc. 1935, 1-10. The major product produced using the conditions of Bouveault and Wahl was found to be diethyl2-oxofurazan dicarboxylate.

U.S. Pat. No. 3,761,510 discloses the preparation of alkyl nitroacetates by reaction of an acyl nitrate and an alkyl acetoacetate in the presence of an acid catalyst at low temperature to form an alkyl nitroacetoacetate intermediate. The alkyl nitroacetoacetate intermediate is cleaved with a nucleophile to form the corresponding alkyl nitroacetate. Although good yield of the alkyl nitroacetate was reported, this process is not a suitable commercial route since it presents a serious safety concern by requiring the preparation and isolation of the potentially explosive acetyl nitrate intermediate.

SUMMARY OF THE INVENTION

It has been discovered that anhydrous nitration of acetoacetate can be accomplished by reacting alkyl acetoacetate and an acid anhydride with nitric acid at low temperatures, optionally in the presence of an acidic catalyst, to obtain high yields of nitroacetoacetates which can be readily cleaved by addition of a nucleophile to form alkyl nitroacetates. The process avoids the isolation of the potentially explosive acetyl nitrate reagent required in some prior art processes.

It is an object of the present invention to provide an improved process for preparing alkyl nitroacetate in high yields.

It is another object of this invention to provide a process for preparing alkyl nitroacetoacetate using alkyl acetoacetate, an acid anhydride and nitric acid in a rapid, safe and simple manner.

Other objects will become apparent from the following detailed description thereof.

DETAILED DESCRIPTION OF THE INVENTION

In accordance with the process of this invention, nitric acid is gradually added to a solution of alkyl acetoacetate and an acid anhydride, optionally in the presence of an acidic catalyst. Nitric acid can be added in concentrated form (99%) or as the standard 70% aqueous solution. Preferably, the rate of addition of nitric acid is a rate sufficient to maintain the reaction temperature below 20° C., most preferably about −15° C. to 5° C.

The production of alkyl nitroacetoacetate in high yields according to the present invention is temperature dependent and must be carried out at low temperatures. Increased amounts of dialkyl-2-oxofuran dicarboxylate an other undesirable side products are formed at higher temperatures. Further, the addition of nitric acid to alkyl acetoacetate and acid anhydride produces an extremely exothermic reaction which creates an unsafe or hazardous condition and results in higher reaction temperatures thereby promoting the formation of undesired side products.

Acid anhydrides useful in the invention include anhydrides of carboxylic acids. Preferably, anhydride of carboxylic acids of up to six carbon atoms are useful, such as acetic anhydride, propionic anhydride, butyric anhydride, hexanoic anhydride and the like. Acetic anhydride is readily available and is preferred. The carboxylic acid anhydride is added in an amount sufficient to create a substantially anhydrous reaction condition, i.e. in an amount sufficient to take up any water present or formed during the reaction. In general, the acid anhydride is used in an excess, up to about 10 mols % of nitric acid to be added.

Alkyl acetoacetates suitable for use in the invention have the formula

wherein R is an alkyl or cycloalkyl group of one to 18 carbon atoms, preferably one to 12 carbon atoms. Suitable R groups include methyl, ethyl, isopropyl, dodecanoyl, stearyl, cyclohexyl and the like.

Suitable acid catalysts which may be used include strong inorganic acids, such as perchloric acid and sulfuric acid; strong organic acids such as p-toluene sulfonic acid and methane sulfonic acid; and Lewis acids such as boron trifluoride, antimony pentafluoride, phosphorus pentafluoride, titanium tetrafluoride, tellurium hexafluoride and tin tetrafluoride. Sulfonic acid cationic exchange resins can also be employed. Several of these resins are commercially available, such as Dowex 50W-X8 of Dow Chemical Co., Amberlite IR 120 of Rohm & Haas Co., Permutit Q of Permutit Co., Nalcite HCR of National Aluminate Co. and Ionac C-240 of American Zeolite Co. Processes for making sulfonic acid resins are described in U.S. Pat. Nos. 2,366,007 and 2,466,675. Weak acids, such as acetic acid and trifluoroacetic acid, are unsuitable as catalysts.

When used, the acidic catalyst is used in a "catalytically effective amount". As used herein, a "catalytically effective amount" is an amount which is capable of catalyzing the nitration of the alkyl acetoacetate. The acidic catalyst should be used in an amount of at least 0.01 mol % to about 10 mol % of the alkyl acetoacetate present. The preferred catalytic amounts are from about 0.1 to about 1.0 mol % based on the alkyl acetoacetate starting material. In the case of the cationic exchange resins, much greater amounts of the catalyst can be present, on the order of from about 1 to about 800 mol % based on the alkyl acetoacetate. Preferably from about 5 to 100 mol % will be employed.

The reaction can be carried out in the presence of an anhydrous diluent if desired. Suitable diluents should be miscible with the reactants and the products and can be lower organic acids such as acetic acid, propionic acid and the like; alkyl ethers such as diethyl ether, methyl ethyl ether and the like; esters such as methyl acetate, ethyl acetate and the like; halogenated solvents such as chloroform, carbon tetrachloride, ethylene dichloride and the like. An excess of the carboxylic acid anhydride can also be employed as the diluent and is preferred.

The alkyl nitroacetoacetate product can be isolated from the reaction mixture by fractionally distilling below about 120° C., preferably below about 100° C. When an acidic catalyst has been used, it is desirable, but not required, to remove the catalyst prior to distillation. When a cationic exchange resin is employed as catalyst, it can be removed by filtering or decanting and reserving for recycle. In a continuous process, the reaction mixture can be passed through a fixed catalyst bed and the product mixture collected, as will be known to one skilled in the art.

Lewis acids do not require neutralization or removal. Other acid catalysts can be removed by neutralizing with a base. Since the alkyl nitroacetoacetates are unstable in the presence of water, the base should be in anhydrous form. Any strong inorganic base is suitable for the neutralization, such as the carbonates, oxides or hydroxides of the alkali or alkaline earth metals. Illustrative bases include sodium hydroxide, potassium hydroxide, calcium oxide, magnesium oxide, sodium carbonate and the like. A sufficient amount of base is added to neutralize the acid catalyst present. The water of neutralization can be taken up for example by excess carboxylic acid anhydride present in the reaction mixture.

Alkyl nitroacetoacetates are unstable in the presence of acids and condense to form dialkyl-2-oxofurazan dicarboxylates. They are highly reactive to nucleophiles such as water and the lower alcohols to form alkyl nitroacetates and acetic acid or its corresponding ester derivative. Basic nucleophiles, such as ammonia, primary and secondary amines, are also reactive with the alkyl nitroacetoacetates to form the corresponding acetamides. Alkyl nitroacetoacetates are stable in the presence of tertiary amines, e.g. triethylamine.

When it is desired to isolate alkyl nitroacetates directly from the reaction mixture, without first isolating the alkyl nitroacetoacetates, a nucleophile can be added directly to the reaction mixture. This reaction can be carried out at ambient temperatures. The catalyst can be removed, if required, as discussed hereinbefore or after addition of the nucleophile. If an acid catalyst is neutralized after addition of a nucleophile, anhydrous conditions are not required.

The desired alkyl nitroacetates are recovered by removing any volatile solvents present, as by flash distillation or evaporation, and fractionally distilling the product mixture at reduced pressures.

The invention will be further illustrated by the following examples, but it is to be understood that the invention is not meant to be limited to the details described therein. In the examples % is by weight.

EXAMPLE I

A solution of 135 ml. of acetic anhydride and 0.295 ml. of concentrated sulfuric acid was prepared. A 100 ml. three-necked-round-bottom-flask equipped with a magnetic stirrer, thermometer and an addition funnel, capped with a drying tube, was charged with 28 ml. of the acetic anhydride solution containing concentrated sulfuric acid. The reaction mixture was cooled to 0° C., and 25.4 ml. of ethyl acetoacetate was slowly added so as to maintain 0°-5° C.

A new addition funnel was put in place and 9.8 ml. of 90% nitric acid was added slowly so as to maintain the temperature between 0°-5° C. (Caution?—The reaction with nitric acid was violently exothermic.) After 90 minutes at a temperature of 0°-5° C., the reaction mixture was added to 200 ml. of ice cold ethanol and stirred for 10 minutes in an ice bath, and then overnight at room temperature. The ethanolic solution was treated with 0.31 gm. of anhydrous sodium carbonate and stirred for ten minutes The mixture was filtered, volatiles removed under vacuum, and finally distilled at 75° C./0.65 mm. to afford a 75% yield of ethyl nitroacetate.

EXAMPLE II

A 250 ml. three-necked-round-bottom-flask equipped with a magnetic stirrer, thermometer and an addition funnel capped with a drying tube was charged with 28 ml. of acetic anhydride. The reaction mixture was cooled to −15° C. and 36.2 ml. of ethyl acetoacetate was slowly added so as to maintain the temperature between −15 to −10° C.

A new addition funnel was put in place and 12.25 ml. of 99% nitric acid was added slowly so as to maintain a temperature of −15° to −10° C. (Caution?—The reaction with nitric acid was violently exothermic.) After 3 hours at −15 to −10° C., a 5 ml. aliquot of the reaction mixture was added to 19 ml. of ice cold ethanol and stirred for 10 minutes in an ice bath and then overnight at room temperature. The yield of ethyl nitracetate was 84%, as determined by gas chromatography, using naphthaline as an internal standard.

EXAMPLE III

A 5 ml. aliquot from the reaction mixture, described hereinabove in Example II, was added to 3.5 ml. of cold ethanol, stirred for 10 minutes and then heated at 40° C. for 2 hours. The yield of ethyl nitroacetate was 78%, as determined by gas chromatography, using naphthaline as an internal standard.

EXAMPLE IV

A solution of 100 ml. of acetic anhydride and 0.11 ml. of concentrated sulfuric acid was prepared. A 15 ml. two-necked-round-bottom-flask equipped with a magnetic stirrer, thermometer and an addition funnel, capped with a drying tube, was charged with 2.5 ml of the acetic anhydride solution containing concentrated sulfuric acid. The reaction mixture was cooled to a temperature between 15° to 20° C. and 2.54 ml. of ethyl acetoacetate was slowly added so as to maintain the temperature between 15° to 20° C.

A new addition funnel was put in place and 1.2 ml. of 90% nitric acid was added slowly so as to maintain temperature between 15° to 20° C. After 2 hours at 15° to 20° C., the reaction mixture was added to 20 ml. of ice cold ethanol and stirred for 10 minutes in an ice bath and then overnight at room temperature. The yield of ethyl nitroacetate was 60%, as determined by gas chromatography, using naphthaline as an internal standard.

We claim:

1. A process for preparing alkyl nitroacetoacetate comprising providing in a reaction vessel a solution of alkyl acetoacetate, a carboxylic acid anhydride and optionally, a catalytically effective amount of an acidic catalyst; introducing into said reaction vessel gradually over the course of the reaction nitric acid at a rate sufficient to maintain the reaction temperature below 20° C.; optionally, removing the acidic catalyst; and recovering the alkyl nitroacetoacetate.

2. The process of claim 1 wherein nitric acid is introduced into said reaction vessel at a rate sufficient to maintain the reaction temperature at about −15° C. to 5° C.

3. The process of claim 1 wherein the alkyl group of the alkyl acetoacetate has from 1 to 18 carbon atoms.

4. The process of claim 1 wherein the acid anhydride is an anhydride of a carboxylic acid having up to about six carbon atoms.

5. The process of claim 1 wherein an acidic catalyst is provided and the catalyst is perchloric acid or sulfuric acid.

6. The process of claim 1 wherein an acidic catalyst is provided and the catalyst is a Lewis acid selected from the group consisting of boron trifluoride, antimony pentafluoride, phosphorupentafluoride, titanium tetrafluoride, tellurium hexafluoride and tin tetrafluoride.

7. The process of claim 1 wherein an acidic catalyst is provided and the catalyst is a sulfonic acid cationic exchange resin.

8. A process according to claim 3 wherein the alkyl acetoacetate is ethyl acetoacetate.

9. A process according to claim 3 wherein the alkyl acetoacetate is methyl acetoacetate.

10. A process according to claim 3 wherein the alkyl acetoacetate is isopropyl acetoacetate.

11. A process according to claim 3 wherein the alkyl acetoacetate is cyclohexyl acetoacetate.

12. A process for preparing alkyl nitroacetate comprising (1) providing in a reaction vessel a solution of alkyl acetoacetate, a carboxylic acid anhydride and, optionally, a catalytically effective amount of an acidic catalyst; (2) introducing into said reaction vessel nitric acid at a rate sufficient to maintain the reaction temperature below 20° C.; (3) optionally, removing the acidic catalyst; (4) adding a nucleophile to the reaction in an amount sufficient to cleave the alkyl nitroacetoacetate; and (5) recovering the alkyl nitroacetate.

13. The process of claim 12 wherein nitric acid is introduced into said reaction vessel at a rate sufficient to maintain the reaction temperature at about −15° C. to 5° C.

14. The process of claim 12 wherein the alkyl group of the alkyl acetoacetate has from 1 to 18 carbon atoms.

15. The process of claim 12 wherein the acid anhydride is an anhydride of a carboxylic acid having up to about six carbon atoms.

16. The process of claim 12 wherein an acidic catalyst is provided and the catalyst is perchloric acid or sulfuric acid.

17. The process of claim 12 wherein an acidic catalyst is provided and the catalyst is a Lewis acid selected from the group consisting of boron trifluoride, antimony pentafluoride, phosphorus pentafluoride, titanium tetrafluoride, tellurium hexafluoride and tin tetrafluoride.

18. The process of claim 12 wherein an acidic catalyst is provided and the catalyst is a sulfonic acid cationic exchange resin.

19. A process according to claim 16 wherein from 0.01 to 10 mols of perchloric or sulfuric acid catalyst is added, based on the mols of alkyl acetoacetate present in the solution.

20. A process according to claim 19 wherein from 0.1 to about 1.0 mol of catalyst is added.

21. A process according to claim 12 wherein the alkyl acetoacetate is ethyl acetoacetate and the nucleophile is ethanol.

22. A process according to claim 18 wherein from 1 to 800 mols of resin is present, based on the mols of alkyl acetoacetate present in the solution.

23. A process according to claim 18 wherein from 5 to 100 mols of the resin is present.

24. A process according to claim 18 wherein the alkyl acetoacetate is ethyl acetoacetate and the nucleophile is ethanol.

25. A process according to claim 12 wherein from 0.01 mol to 10 mols of an acidic catalyst is provided, based on the mols of alkyl acetoacetate present in the solution.

26. A process according to claim 25 wherein from 0.2 to about 1.0 mol of catalyst is added.

27. A process according to claim 26 wherein the alkyl acetoacetate is ethyl acetoacetate and the nucleophile is ethanol.

* * * * *

UNITED STATES PATENT AND TRADEMARK OFFICE
CERTIFICATE OF CORRECTION

PATENT NO. : 5,162,572

DATED : November 10, 1992

INVENTOR(S) : Sheldon B. Markofsky

It is certified that error appears in the above-indentified patent and that said Letters Patent is hereby corrected as shown below:

Column 1, line 48, change "diethyl2-oxofurazan" should read -- diethyl-2oxofurazan--.

Signed and Sealed this

Ninth Day of November, 1993

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.  : 5,162,572
DATED       : November 10, 1992
INVENTOR(S) : Sheldon B. Markofsky It is certified that error appears in the above-indentified patent and that said Letters Patent is hereby corrected as shown below:

In the Abstract:

At Line 3, change "alkyl nitroacetate" to --alkyl acetoacetate--.

Col. 4, line 53, change "naphthaline" to --naphthalene--.

Col. 5, line 13, change "naphthaline" to --naphthalene--.

At column 4, line 51, change "nitracetate" to --nitroacetate--.

Signed and Sealed this

Twelfth Day of April, 1994

*Attest:*

BRUCE LEHMAN

*Attesting Officer*

Commissioner of Patents and Trademarks